United States Patent [19]
Deslauriers et al.

[11] Patent Number: 5,255,678
[45] Date of Patent: Oct. 26, 1993

[54] MAPPING ELECTRODE BALLOON

[75] Inventors: Antoine Deslauriers, Montreal; Pierre Savard, Ste-Therese; Pierre Pagé, Terrebonne; René Cardinal, Outremont; Josée Rousseau, Montreal, all of Canada

[73] Assignee: Ecole Polytechnique, Quebec, Canada

[21] Appl. No.: 719,006

[22] Filed: Jun. 21, 1991

[51] Int. Cl.$^5$ .............................................. A61B 5/04
[52] U.S. Cl. ...................................... 128/642; 607/122
[58] Field of Search ................ 128/642, 784, 785, 786

[56] References Cited

U.S. PATENT DOCUMENTS

| | | | |
|---|---|---|---|
| 4,519,403 | 5/1985 | Dickhudt | 128/786 X |
| 4,552,127 | 11/1985 | Schiff | 128/642 X |
| 4,649,924 | 3/1987 | Taccardi | 128/642 |
| 4,699,147 | 10/1987 | Chilson et al. | |
| 4,961,738 | 10/1990 | Mackin | 128/6 X |

OTHER PUBLICATIONS

"Endocardial Mapping by Simultaneous Recording of Endocardial Electrograms During Cardiac Surgery for Ventricular Aneurysm" by Bakker et al., JACC vol. 2, No. 5, Nov. 1983, pp. 947-953.
"Endocardial Activation Mapping and Endocardial Pace-Mapping Using a Balloon Apparatus", by Fann et al., AM J Cardiol, vol. 55, 1985, pp. 1076-1083.
"A New Intraoperative Approach for Endocardial Mapping of Ventricular Tachycardia", by Mickleborough, J. Thorac Cardiovasc Surg., vol. 95, 1988, pp. 271-274.
"Potential Distribution Mapping: New Method for Precise Localization of Intramural Septal Origin of Ventricular Tachycardia", by harada et al., Circulation vol. 78, No. 5, Nov. 1988 (suppl. III), III-137-147.
"Intra-Atrial Reentry as a mechanism for Atrial Flutter Induced by Acetylcholyne and Rapid Pacing in the Dog", by Allessie et al., Circulation vol. 70, No. 1, Jul. 1984, pp. 123-125.

Primary Examiner—Lee S. Cohen
Assistant Examiner—Samuel Gilbert
Attorney, Agent, or Firm—Samuel Meerkreebs

[57] ABSTRACT

An electrode balloon for use in anatomical cavities, such as cardiac chambers, to pick up bioelectrical signals from the walls thereof simultaneously in a multitude of sites for the mapping of the activation potentials thereof comprises an inflated tight rubber balloon having an opening at a proximal end thereof communicating with a filling tube which defines apertures for dispensing fluid in the rubber balloon. An extensible knitting which covers the rubber balloon is provided with a plurality of electrode heads distributed thereon to contact the walls of the cavity when the rubber balloon is inflated by a fluid conveyed therein through the tube. Insulated electrical conductors connect the electrodes to a signal recording and processing device. A tutor extending longitudinally through the rubber balloon and further extending therefrom to form a handle includes two separate longitudinal compartments which constitute the filling tube and a compartment for receiving an intubation guide which serves to guide the knitting covered rubber balloon into the cavity. The electrodes are hollow balls sewn to the knitting and joined to the conducting wires with weldless joints. The knitting is patterned in order to confer to the inflated rubber balloon the shape of the cavity being studied. The electrode balloon is adapted, for instance, to study the left and right ventricles by way of its the insertion through an incision in their respective auricles and through the mitral and tricuspid valves thereof, respectively.

46 Claims, 4 Drawing Sheets

MAPPING ELECTRODE BALLOON

BACKGROUND OF THE INVENTION

1. Field of the Invention

The present invention relates to electrode balloons for picking up bioelectrical signals from the cavities of the heart for their simultaneous recording in a multitude of sites followed by the mapping of the endocardial activation potentials. More particularly, the present invention relates to an electrode balloon having a structure which is easily adaptable to any one of the cardiac chambers and which can be used in the right or left ventricles of the heart without resorting to a ventriculotomy.

2. Description of the Prior Art

There exists many types of electrode systems for recording endocardial activation potentials. Before the advent of simultaneous recording in a multitude of sites, the bioelectrical signals were taken from one site at a time using a hand-held probe. A long sequence of regular heartbeats or of constant morphology was necessary in order to have time to cover all the necessary sites required for making such a mapping.

Although it is still used occasionally, the hand-held probe has been replaced by devices carrying a multitude of electrodes which require two or three heartbeats for the mapping. Amongst these systems, we find endocardial balloons with spherical balls or plaquettes having a high density of electrodes thereon. The former permits a global view, for instance, of the endocardium of the left ventricle, while the latter provides in a more limited region thereof a multitude of lectures in very near sites. Such a concentration enhances the resolution and permits the grasping of very fine electrophysiological mechanisms. There also exists needles carrying a series of aligned electrodes that are inserted through the cardiac muscles in order to pick up signals from the endocardium.

U.S. Pat. No. 4,699,147 (issued on Oct. 13, 1987 to Chilson et al.) discloses a probe provided with a plurality of electrodes for intraventricular cardiac mapping. The probe comprises a catheter and four elongated wire assemblies received therein. Each wire assembly comprises a tubing, six insulated wire conductors received in the tubing, and a central core wire which is stiff but yet flexible. A proximal connector mounted on each tubing is connected by way of the six insulated wire conductors to six spaced apart sleeve electrodes mounted on each wire assembly at a distal end portion thereof. A portion of each core wire in the distal end portion of one of the wire assemblies can be caused to assume a desired configuration after distal end portions of the wire assembly are moved from a retracted position within the catheter to a position where the distal end portions are extended from the catheter and where the core wires can be caused to assume the desired configuration to form an elliptical envelope. In the retracted position, the wire assemblies are parallel and closely spaced apart thereby allowing the catheter to be inserted into an artery or a vein to place the distal end portions of the wire assemblies in a cardiac chamber where they can be extended to create the elliptical envelope. The distal end portions of the wire assemblies can then be incrementally rotated while electrical potentials are measured and recorded at different points along the surface of an endocardial wall of a cavity of the heart, such as a ventricle, that come into contact with the sleeve electrodes. Such a probe thus necessitates that the elliptical end portion thereof be rotated to measure a sufficient amount of points along the inner wall of the chamber. Such a rotation prevents a recording of all of the electrical potentials simultaneously in a single heartbeat. The shape of the elliptical envelope depending only on the central core wire contained in each one of the wire assemblies does not adapt itself to slightly different shapes and volumes of the cardiac chamber being studied. Such discrepancies in the shape and the volume of the cavity will impede the proper contact of all the sleeve electrodes with the endocardium. Also, the amount of recording sites and the distribution thereof are limited. It is noted that the above probe is non invasive, meaning that the manipulation of this catheter does not require the opening of the rib cage. Therefore, the previous disadvantages are quite acceptable for a non invasive probe.

Electrode balloons were then developed in order to be able to record electrical potentials simultaneously on the whole surface of the cardiac chamber being studied. Such electrode balloons are used in the operating room and are thus considered invasive.

The first type of ball-type balloons are used on humans in the operating room to record a plurality of endocardial electrograms simultaneously during cardiac surgery on patients subject to aneurysmectomy and/or endocardial resection. In use, the balloon after having been inserted into a ventricle is inflated so as to bring the sensor electrodes into contact with the endocardial surface thereof. Obviously, this operation is carried out after extracorporeal circulation has been started so as to empty the heart of blood. After the beginning of tachycardia, which is induced by programmed stimulation should it not be present naturally at the time of the operation, the signals picked up by the sensor electrodes are stored and analyzed so as to determine the electrode which was activated first. The operation takes between two and five minutes.

To date, two such electrode balloons inserted by a ventriculotomy have been subject of publications. A description of these balloons follows hereinbelow.

The first balloon called the Amsterdam balloon was disclosed in the article "Endocardial Mapping by Simultaneous Recording of Endocardial Electrograms During Cardiac Surgery for Ventricular Aneurysm" by Bakker et al., JACC Vol. 2, No. 5, November 1983, pages 947-953. The Amsterdam balloon is composed of two superposed latex membranes. The inner membrane represents the tight compartment whereas the outer membrane carries the sensor electrode spherical balls.

The concept of the Amsterdam balloon exploits the latex not for its elasticity but for its plane and smooth surface which facilitates its insertion into the studied cardiac chamber. The balloon, flaccid at the beginning, is inflated after introduction until it reaches the form in which it was molded. At that format, the thick latex is just taut, and not really stretched, with the electrode distribution being regular to permit extrapolation of their anatomical localization when they are hidden. Between that format, the material is a bit flaccid and beyond that same format, it stretches irregularly in view of caprices of the latex. Consequently, this balloon cannot adjust itself in all cases to various and different cavity volumes, whereby the spreading out of the electrodes can have distortions in its regularity.

The Amsterdam balloon has to be introduced in the ventricle by way of an incision in the aneurysm. In cases where a ventriculotomy is not required, the Amsterdam balloon does not have the structural characteristics that would allow it to be positioned in the ventricle while preserving the same.

The second electrode balloon, conceived for animal experimentation on the dog, was disclosed by Fann et al. in the article "Endocardial Activation Mapping and Endocardial Pace-Mapping Using a Balloon Apparatus", Am J Cardiol, Vol. 55, 1985, pages 1076-1083. In this balloon, referred hereinafter as the Chicago balloon, a tight latex chamber is covered with a not very extensible netting that carries sensor electrode balls which are mounted in pairs on inserts for a bipolar recording. The balloon is inserted directly in the left ventricle by sliding it through a guide tube. As for the Amsterdam balloon, the Chicago balloon is therefore inserted in the ventricle by way of a ventriculotomy.

A third electrode balloon, referred to as the Toronto balloon, was disclosed by Mickleborough in the article entitled "A New Intraoperative Approach for Endocardial Mapping of Ventricular Tachycardia", J Thorac Cardiovasc Surg, Vol. 95, 1988, pages 271-274. This electrode balloon for humans was designed to be inserted in the left ventricle without having recourse to a ventriculotomy as it is insertable through the left auricle and the mitral valve of the heart. Its construction is very similar to that of the Chicago balloon except that the silver electrode balls thereof are pierced to be sewn one by one to an expendable mesh which covers a double-layered latex balloon. This fixation mode is well adapted to the restraints inherent with an insertion through the mitral valve.

The following documents disclose apparatuses for the endocardial mapping of the other cardiac chambers, that is the right ventricle and the left and right auricles.

Multielectrode endocardial probes for the left and right ventricular cavities are described by Harada et al. in the article entitled "Potential Distribution Mapping: New Method for Precise Localization of Intramural Septal Origin of Ventricular Tachycardia", Circulation Vol. 78, No. 5, Nov. 1988 (suppl. III), III-137-147. This probe is made from a foam rubber cast carrying a set of silver electrode heads. However, this probe, hereinafter referred to as the St-Louis probe, was conceived for animal experimentation wherein concessions can be made regarding the insertion and withdrawal constraints. The probe not being entirely compressible, a wider opening of the auricle as well as rougher manipulations are necessary in order to set the probe in place and to withdraw it. On the other hand, withdrawal of the probe is not a preoccupation as it is withdrawn from the heart after dissection thereof.

The above probe is the only electrophysiological probe designed for the right ventricle found to date in the scientific literature. According to the above article in which it is described, the St-Louis probe has a shape that is well adapted to the right ventricle. On the other hand, the probe is limited as indicated hereinabove to animal experimentation.

Only one multielectrode electrophysiological probe model for the auricles has been disclosed to date in the scientific literature. This probe, hereinafter referred as the Maastricht probe, is described by Allessie et al. in "Intra-Atrial Reentry as a Mechanism for Atrial Flutter Induced by Acetylcholyne and Rapid Pacing in the Dog", Circulation Vol. 70, No. 1, July 1984, Pages 123-125. It consists of two rigid casts made from a polymeric resin which are strawberry and egg-shaped respectively for the left and right auricles. Each mold comprises 480 electrodes. These probes were designed specifically for animal experimentation whereby they are introduced in the auricles by a large incision through the underlying ventricles. Such incisions are not allowed for humans when the ventricle has to be preserved. Made from a rigid material, these probes are not compressible whereby larger openings and rougher manipulations are necessary for the insertion and withdrawal thereof. Moreover, these probes do not offer any latitude regarding various size auricles. On the other hand, such a construction allows for the grafting thereto of a large density of electrodes.

SUMMARY OF THE INVENTION

It is therefore an aim of the present invention to provide an electrode balloon having a universal construction adaptable to any one of the cavities of the heart.

It is also an aim of the present invention to provide an electrode balloon having a novel electrode carrier.

It is a further aim of the present invention to provide an electrode balloon wherein the electrode carrier is a knitting.

It is a still further aim of the present invention to provide an electrode balloon having a shape conferred by the knitting.

It is still a further aim of the present invention to provide different knitting patterns for the various cardiac chambers.

It is still a further aim of the present invention to provide a knitting for a particular one of the cardiac chambers which has a pattern adapted to confer to the electrode balloon a shape that will allow the same to contact when expanded the inner wall of the cardiac chamber for various volumes and shapes of the latter.

It is a still further aim of the present invention to provide a knitting and therefore a balloon which is compact when deflated to facilitate the insertion thereof into the cardiac chamber and wherein the knitting when inflated expands with regularity, moderation and reproducibility.

It is a still further aim of the present invention to provide an electrode balloon wherein the connection of the electrode heads carried by the knitting to the conductive wires is weldless.

It is a still further aim of the present invention to provide electrode balloons for the left and right ventricles that can be inserted therein respectively by way of the left auricle and of the mitral valve and by way of the right auricle and of the tricuspid valve, without resorting to ventriculotomies.

A construction in accordance with the present invention comprises an electrode balloon for use in anatomical cavities to pick up bioelectrical signals from walls thereof simultaneously in a multitude of sites for the mapping of activation potentials thereof. The electrode balloon comprises an inflatable tight member which defines a chamber and which has an opening at a proximal end thereof in connection with a flexible tube means. An extensible cover means which covers at least the chamber is provided with a plurality of sensor electrodes distributed thereon to contact the walls of the cavity when the inflatable member is inflated by a fluid conveyed through the tube means into the chamber. Insulated electrical conductors are connected to the sensor electrodes and to means for recording and processing the signals picked up thereby. A flexible tutor means extends within the chamber from a distal end of the inflatable member through and past the proximal end thereof to provide the electrode balloon with a handle means. The tutor means is adapted to receive therein a flexible intubation guide means for guiding the inflatable member into the cavity.

In a further construction in accordance with the present invention, the tube means is integral with the tutor means at least the length thereof interior of the chamber. The tube means and the tutor means thus define two separate elongated compartments for respectively receiving the fluid and the intubation guide means. At least one aperture is provided in the tube means within the chamber in order to dispense the fluid provided therein in the chamber.

In a still further construction in accordance with the present invention, the inflatable member comprises a rubber balloon, the cover means is a knitting, and the intubation guide means is a malleable stem.

In a still further construction in accordance with the present invention, each one of the sensor electrodes is a hollow ball mounted exteriorly to the knitting. A pair of openings are defined diametrically in the hollow ball to receive therethrough a thread means. The thread means passes through the knitting adjacent the hollow ball whereby the hollow ball is secured to the knitting by the thread means which is knotted intermediate the knitting and the rubber balloon.

In a still further construction in accordance with the present invention, a slot is defined in a portion of the hollow ball facing the knitting and at least partly bearing thereagainst. The electrical conductor passes through the slot and has a bared free end located in the hollow ball which contacts an inner surface of the hollow ball. The electrical conductor is knotted within the hollow ball adjacent the slot thereby securing the bared free end thereof inside the hollow ball and ensuring a contact therebetween. The electrical conductor extends from the hollow ball through the knitting, past the proximal end of the rubber balloon and towards the means for recording and processing the signals picked up by the sensor electrodes.

Another construction in accordance with the present invention comprises an electrode balloon for use in anatomical cavities for picking up bioelectrical signals from walls thereof simultaneously in a multitude of sites for the mapping of activation potentials thereof. The electrode balloon comprises an inflatable tight member defining a chamber, a flexible filling means connected to the chamber, an extensible knitting constituted of closely stitched fine threads covering at least the chamber and provided with a plurality of sensor electrodes distributed thereon for contacting the walls of the cavity when the inflatable member is inflated by a fluid conveyed through the filling means into the chamber. A conductor means is connected to the sensor electrodes and is adapted for connection to a means for recording and processing the signals picked up thereby. A flexible handle means extends from the chamber for guiding the inflatable member into the cavity.

Also in accordance with the present invention, there is provided a method for picking up bioelectrical signals from the walls of anatomical cavities simultaneously in a multitude of sites for the mapping of activation potentials thereof. The method comprises a first step of providing an electrode balloon which comprises an inflatable tight member defining a chamber and having an opening at a proximal end thereof in connection with a flexible tube means. An extensible cover means which covers at least the chamber is provided with a plurality of sensor electrodes which are distributed thereon. Insulated electrical conductors are connected to the sensor electrodes and to a means for recording and processing the signals picked up thereby. A flexible tutor means extends within the chamber from a distal end of the inflatable member through and past the proximal end thereof for providing the electrode balloon with a handle means. The method also comprises the step of introducing in the tutor means a flexible intubation guide for guiding the inflatable member into the cavity, the step of supplying a liquid through the tube means in the chamber for inflating the inflatable member, whereby the sensor electrodes contact the walls of the cavity, and the step of picking up by way of the sensor electrodes the bioelectrical signals of the walls of the cavity simultaneously in a multitude of sites.

Further in accordance with the present invention, there is provided a method for picking up bioelectrical signals from the walls of anatomical cavities simultaneously in a multitude of sites for the mapping of activation potentials thereof. The method comprises a first step of providing an electrode balloon which comprises an inflatable tight member defining a chamber with a flexible filling means being connected to the chamber. An extensible knitting constituted of closely stitched fine threads which covers at least the chamber is provided with a plurality of sensor electrodes which are distributed thereon. Conductor means are connected to the sensor electrodes and to a means for recording and processing the signals picked up thereby. A flexible tubular handle means extends from the chamber. The method also comprises the step of introducing in the handle means a flexible intubation guide for guiding the inflatable member into the cavity, the step of supplying a liquid by way of the filling means in the chamber for inflating the inflatable member, whereby the sensor electrodes contact the walls of the cavity, and the step of picking up by way of the sensor electrodes the bioelectrical signals of the walls of the cavity simultaneously in a multitude of sites.

The electrode balloon according to the present invention is an inflatable probe used in the surgical treatment of cardiac arrhythmias such as ventricular tachycardias, and in cardiac electrophysiological studies of the animals. This probe simultaneously collects bioelectrical signals in a multitude of sites distributed on the internal surface of the heart, meaning on the endocardium. The signals are forwarded to a computer which interprets these punctual readings and makes out maps illustrating the propagation of the electrical impulse waves which is responsible for the cardiac rhythm (endocardial activation potentials).

In a scientific point of view, the maps are used to study the electrophysiological mechanism of the heart, whereas in a therapeutic point of view, that is in the operating room, the maps allow for a rapid and precise localization of the arrhythmogenic areas so as to neutralize them thereafter.

With respect to the left ventricle, for instance, an incision of the left auricle or of the left ventricle of the heart allows the probe plugged to a computer to be introduced in the left ventricle and to then be inflated so that the entirety of the pick-ups, or electrode heads, distributed on its surface contact the endocardium. Electrophysiological signals of normal or pathological cardiac rhythms can then be recorded after which the probe is deflated and then withdrawn from the ventricle in order to proceed with the interpretation of the mapping and with the following operations.

The anatomical correspondence of the endocardial activation mappings is established by way of the balloon of electrodes in place in the ventricle. For doing so, the electrodes are numbered in relation with guiding marks grafted to the exterior knitting of the balloon apparatus.

The choice of the inflatable system used depends on the insertion and retraction restraints, and also on the amplitude of the spreading of the electrodes which is adapted to different volumes of intracardiac cavities. The originality of the present electrode balloon lies in its ability to overcome the insertion restraints inherent to the introduction of the electrode balloon in either one of the ventricles by way of its respective auricle, and in its adaptability using the same basic structure to the different cardiac chambers.

The present electrode balloon has been conceived to be introduced, for example, in the left ventricle by way of the left auricle and of the mitral valve, instead of by a ventriculotomy as it is normally achieved. By doing so, we avoid perturbing the electrophysiological behavior of the ventricle before it has been observed and characterized. Furthermore, this allows the preservation of the ventricle of certain patients who do not require a ventriculotomy.

The insertion by the left auricle is opposed by many restraints:

a) the heart of the patient is deep in the open rib cage and the incision of the auricle through which the probe is inserted is located behind the heart; the run or the path of the probe towards the heart is therefore congested and the approach must be done from a difficult angle;

b) the diameter of the passage is limited at the left auricle incision level and at the mitral valve level;

c) the mitral valve cordages, the papillary muscles and the trabeculations of the left ventricle all represent obstacles to the insertion;

d) the contact with the intracardiac walls offers a resistance to the sliding of the apparatus along its path; and e) by forcing the probe, we risk perforating a wall of the heart or damaging the mitral valve cordages.

Therefore, the present endocardiac probe is an inflated balloon carrying electrode heads distributed on the surface thereof. A handle extends from the balloon and is integral to a filling tube of the balloon. There is also an intubation guide compartment and a conducting wiring harness.

Functionally, we distinguish the electrode system, the adduction system for the electrodes and the tutor.

The electrode system comprises the electrode heads or bearings of spherical shape, the knitting which carries these electrode heads, the conducting wires which converge in a bundle and the electric connectors.

The adduction system for the electrodes against the cavity wall is an inflated tight compartment which comprises a single or double rubber balloon, a tube for filling and emptying the balloon, one or two standard valves to which a syringe can be grafted for this filling, and a pressure gauge.

The tutor on which the balloon is mounted reinforces the structure in order to facilitate the manipulations during the insertion. It is a flexible tube which can be rigidified and which is formed by the introduction therein of an intubation guide of appropriate malleability. The tutor extends from the tip to the base of the balloon and then forms the handle of the probe. The flexible tube includes two distinct canals, one of which is the intubation guide compartment whereas the other is the aforementioned filling tube of the tight compartment.

The knitting which carries the electrodes envelopes or surrounds the rubber balloon. By also enveloping parts of the tutor and of the conducting wiring harness which are juxtaposed, the knitting combines these two parts while providing the handle with a non-slipping grip. The knitting is solidly attached to the tutor by way of a seam.

The probe is plugged to the computer system at the connector level.

BRIEF DESCRIPTION OF THE DRAWINGS

Having thus generally described the nature of the invention, reference will now be made to the accompanying drawings, showing by way of illustration a preferred embodiment thereof, and in which.

DESCRIPTION OF THE PREFERRED EMBODIMENTS

Figure 1:
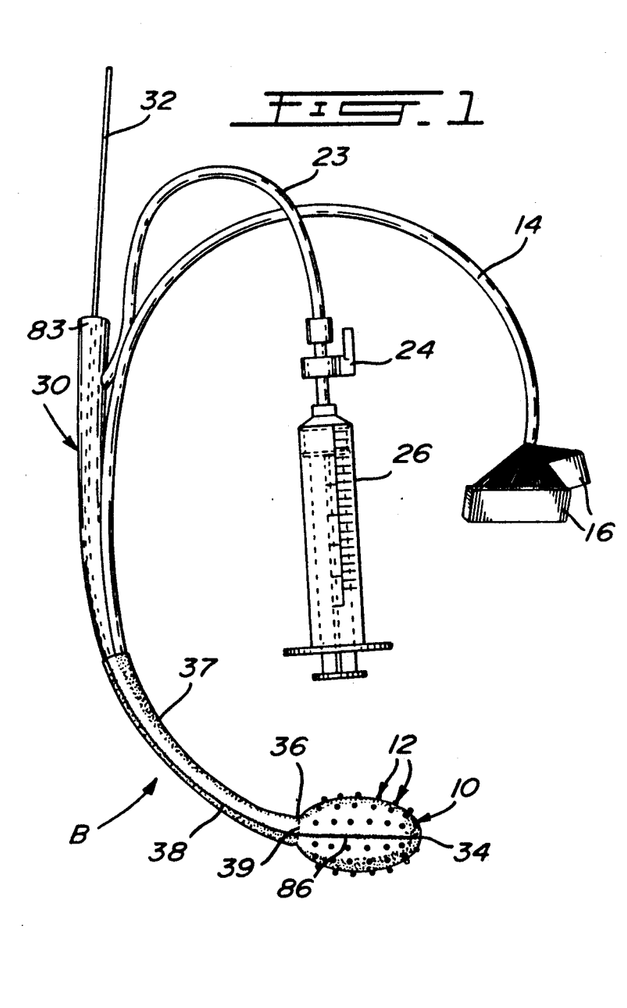
FIG. 1 is a perspective view of an electrode balloon in accordance with the present invention.
Figure 3:
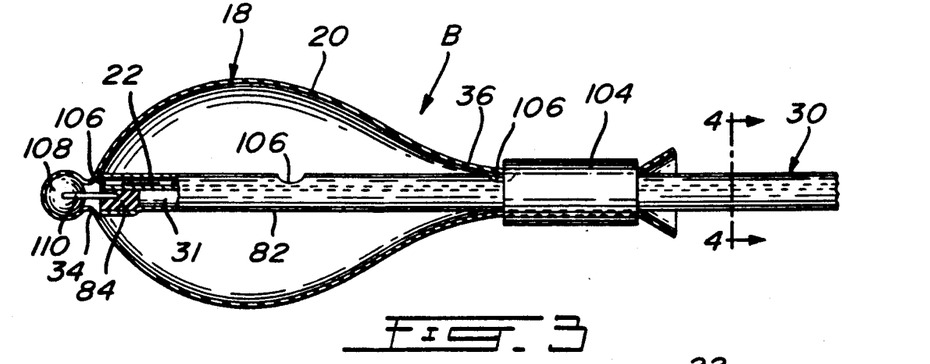
FIG. 3 is a longitudinal cross-section of the tight compartment of the electrode balloon.

FIGS. 1 and 3 illustrate an endocardial electrode balloon B in accordance with the present invention. In the electrode balloon B, we distinguish functionally the electrode system, the electrode adduction system and the tutor.

The electrode system comprises a knitting 10, electrode heads 12 which are carried by the knitting 10, conducting wires 88 which 14 converge in a harness 14, and connectors 16.

The electrode adduction system comprises an inflatable tight compartment 18 which includes a single rubber balloon 20, a tube 22 for filling and emptying the balloon 20 which is connected by way of an extension 23 to one or two standard three-way valves 24 to which a syringe 26 and a pressure gauge (not shown) can be grafted.

A tutor 30, on which the balloon 20 is mounted, reinforces the structure to facilitate the manipulations during the insertion of the balloon B in a cardiac chamber, as will be described in details hereinbelow. The tutor 30 is a flexible tube which can be rigidified and which is formed by introducing in a compartment 31 thereof an intubation guide 32 of appropriate malleability. The tutor 30 extends from a tip 34 of the balloon 20 to a base 36 thereof and then forms a handle 37 of the probe.

The knitting 10 which carries the electrodes 12 envelopes or surrounds the rubber balloon 20. By also enveloping parts of the tutor 30 and of the conducting wiring harness 14 which are both juxtaposed, the knitting 10 combines these two parts while providing the handle 37 with a nonslipping grip. The knitting 10 is solidly attached to the tutor 30 by way of junction seams 38 complemented by a constriction seam 39 at the base 36 of the balloon 20. Alternatively, the knitting 10 can be glued to the tutor 30 along the length of the handle 37.

Figure 2:
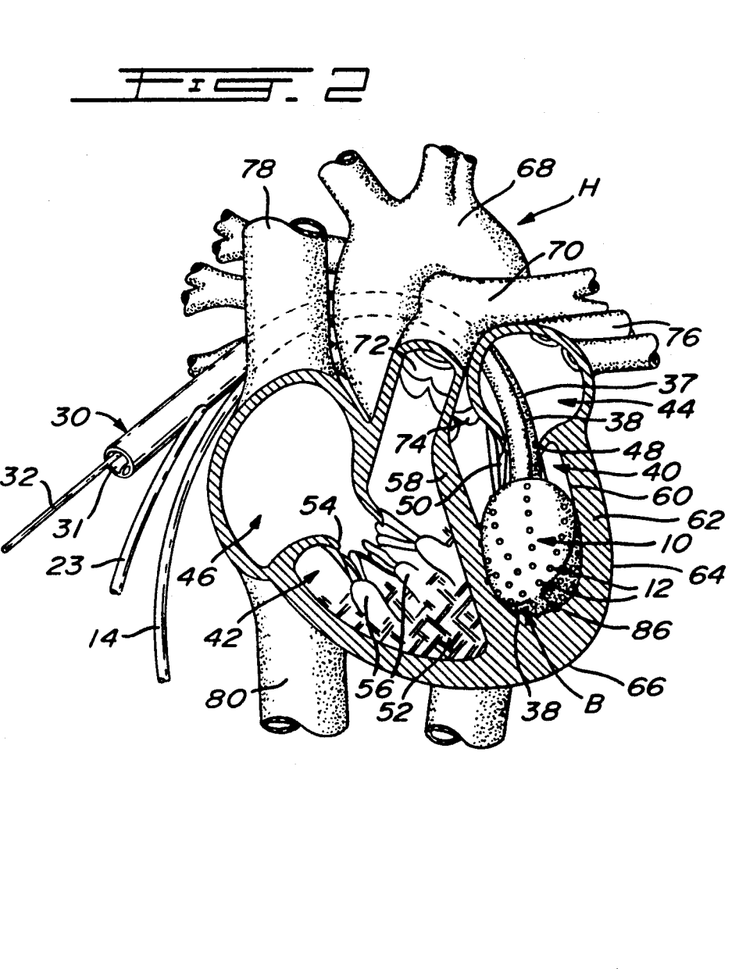
FIG. 2 is a front view in cross-section of the human heart showing the cavities thereof and further illustrating the electrode balloon in place in the left ventricle.

FIG. 2 illustrates the electrode balloon B in position in a left ventricle 40 of a heart H. The other parts of the heart H are identified on FIG. 2 as follows:

42: right ventricle
44: left auricle
46: right auricle
48: mitral valve
50: mitral valve cordages
52: trabeculation
54: tricuspid valve
56: papillary muscle
58: ventricular septum
60: endocardium
62: myocardium
64: epicardium
66: apex of heart
68: the aorta
70: pulmonary artery
72: pulmonary valve
74: aortic valve
76: pulmonary veins
78: superior vena cava
80: inferior vena cava Now referring generally to FIGS. 1 to 3, the tutor 30 which is made of PVC is introduced in the heart H by holding it by the handle 37 and by pushing it to the interior after having given the tutor 30 an appropriate shape.

For minimizing the insertion resistance, the knitting 10 must be well stretched. That is why a thrust tutor 82, which is the part of the tutor 30 and which enters and traverses the interior of the balloon 20 is long enough to keep the balloon 20 and the knitting 10 stretched.

Exteriorly of the balloon 20, the tutor 30 forms the handle 37 and in its prolongation, its two compartments, that is the filling tube 22 and the intubation guide compartment 31, separate one from the other in a funnel 83 which is the extension of the intubation guide compartment 31 and in the extension 23 of the filling tube which is a prolongation of the tight compartment 18.

The intubation guide 32, or the rigidification stem, is a malleable stem of plastic or metal which slides in the intubation guide compartment 31 until it reaches the tip 34 of the balloon 20 in view of giving to the tutor 30 a curvature while providing it with an appropriate rigidity for insertion in the heart H. On the other hand, this rigidity must not be excessive in order not to pierce a wall of the heart H. The intubation guide compartment 31 is sealed at its extremity, that is at the tip 34 of the balloon, by a rubber plug 84 which prevents air from circulating or entering the heart H, and on which the intubation guide 32 abuts.

The knitting 10 which supports the electrode heads 12 and cover the balloon 20 is of a resistant commercial material, made of nylon and elastomer.

The intrinsic structure and the elastomer construction of the knitting 10 provide the latter with an elasticity whereby little material is required for covering the balloon 20. When the balloon 20 is deflated, the knitting 10 will stay well stretched. We therefore avoid resistance to the insertion which would be produced by an excess of knitting.

Since the knitting 10 stretches in a very even way, without torsion, the electrode heads 12 also spread out very evenly upon the partial or complete inflating of the balloon 20, in spite of the fact that the rubber balloon 20 which underlies the knitting 10 may spread out with irregularities. This way, the electrode balloon B offers a functional range of volumes to thus adjust itself to variable sizes of anatomical cavity for which it is intended. This is the advantage of the knitting 10 in relation to an elastomer membrane (latex, rubber or the like) for supporting the electrodes. Such an even spreading out of the electrodes 12 is necessary to estimate the location of the electrodes on the endocardium 60 when the balloon 20 is in place and when the ventricle and, more particularly, in this illustrated preferred embodiment, the left ventricle 40, is not yet open.

The knitting 10 is assembled with seams, one of which is more distinct as it serves as a guiding mark seam 86 for identifying the electrodes 12 which are numbered in relation thereto and for the localization thereof on the endocardium 60. Other guiding mark seams can be attached thereto, as a knot to identify the order of numeration of the electrodes 12.

The assembly seams 38 and 86 do not extend to the tip 34 of the balloon 20 in view of not weakening this section of the knitting 12 which is solicited by the thrust of the tutor 30.

The knitting 10 offers the possibility of varying the disposition and the number of electrodes 12 on its surface contrarily to a netting or a mesh carrying the electrodes, as the latter are limited to certain configurations due to the stitches or the meshes thereof. In the case of the probe herein presented, the regular disposition of the electrodes 12 in rows and in columns permits a more easy identification thereof, especially for those which are located on a hidden face of the balloon 20 and for which we must extrapolate the position on the endocardium 60.

Figures 4, 5:
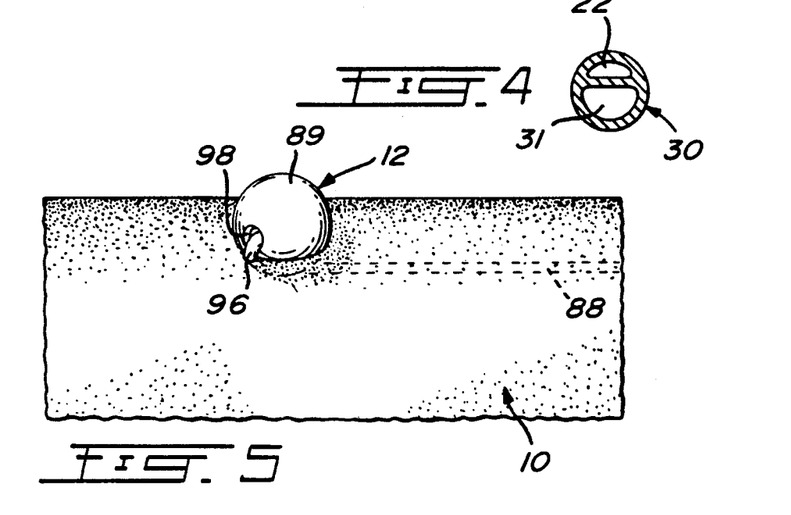
FIG. 4 is a cross-section taken along lines 4—4 of FIG. 3 illustrating the two separate canals in the tutor.
FIG. 5 is a perspective view showing an electrode head mounted to the knitting of the electrode balloon.
Figure 6:
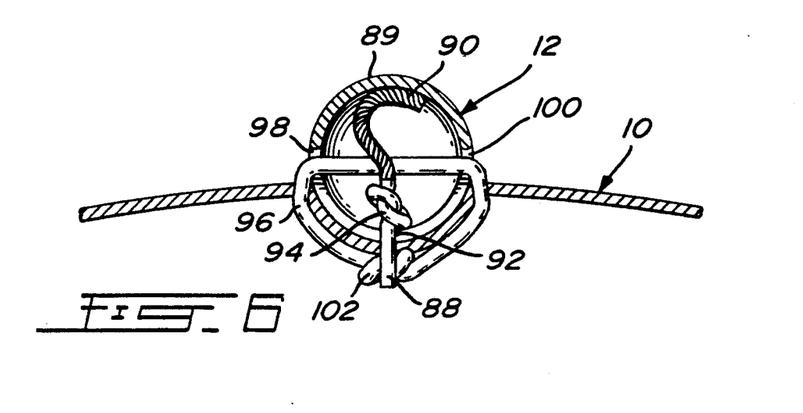
FIG. 6 is a cross-sectional view showing the attachment mode of the electrode head to the knitting.

Now referring to FIGS. 5 and 6 regarding the electrode heads 12, standard stainless steel wires 88 surrounded by an insulating material carry the electrical information taken from the endocardium 60. At the extremity in contact with the endocardium 60, each wire 88 carries one of the electrode heads 12 which has a role of a sensor or a pick up and of a junction of the electrodes 12 to the knitting 10. At the other extremity, each wire 88 ends with a crimp type contact in the standard connectors 16. In the case illustrated in FIG. 1, the balloon 20 carries sixty-four unipolar electrodes 12, plugged in numerical order in the two connectors 16.

The electrode heads 12 at the pick-up extremity of the wires 88 comprise stainless steel hollow balls 89 mounted exteriorly to the knitting 10 as described hereinafter. To each ball 89 is attached a conducting wire in the following way: a knotted and bare extremity 90 of the conducting wire 88 is introduced in the ball through a slot 92 defined on an inward portion thereof which is firstly open and then closed to secure the wire by an imprisoned knot 94 in the cavity of the ball 89 thereby ensuring the electrical contact between the bare part 90 of the wire 88 and the internal wall of the ball 89. This is therefore a weldless joint. The conducting materials which are in contact being identical, we avoid junction potentials. Stainless steel is a conductor which offers a certain resistance (impedance) but it provides a satisfactory ratio "signal/noise".

Each ball 89 which is positioned on the knitting 10 with the wire 88 passing therethrough is then attached to the knitting 10 by a connection thread 96 which goes through a series of times a pair of diametrically opposed apertures 98 and 100 in order to extend across the ball 89 and through the knitting 10 with the connection thread 96 being knotted and glued on itself on the internal surface of the knitting 10 as indicated by numeral 102. This way, the ball stays solidly fixed independently of the conducting wire 88 which is attached thereto. This is a critical point as it would be ill-fated to lose a ball in the circulatory system of the patient. Moreover, this fastening mode of the balls 89 does not allow for their movement on the knitting 10 which would produce imprecisions in the reading of the endocardial bioelectrical signals.

The protrusions formed by the balls 89 on the knitting 10 ensure a proper contact with the endocardium 60, in spite of the surface irregularities thereof (e.g. trabeculations 52, papillary muscles 56).

All the conducting wires 88 are longitudinally inserted between the knitting 10 and the balloon 20 parallel one to the other until the base 36 of the balloon 20. Then, when the balloon 20 is inflated and the electrodes 12 spread out, the conducting wires 88 remain in place without entangling. Otherwise, the conducting wires 88 would risk breaking or restraining the inflating of the balloon 20. When an electrode 12 is defective and has to be replaced, it is possible to access it by the point of emergence of the wire 88 associated therewith at the surface of the knitting 10 without having to disassemble the latter.

From the handle 37, the conducting wires 88 join in a supple plastic sheath into the compact harness 14, until the connectors 16.

The quality of the gathered bioelectrical signals and the reproducibility of the results collected demonstrate the validity and the reliability of this electrode concept.

The tight compartment 18 includes the balloon 20 and the adjoining canalization tube 22 which serves to inflate and evacuate the balloon 20. The construction of the tight compartment 18 is described in details hereinafter.

The balloon 20 which is made of a rubber membrane is tightened against the tutor 30 by way of a silicone elastic ring 104 (FIG. 3). This joint is made tight by gluing.

The filling tube 22 extends the length of the tutor 30 and communicates with the interior of the balloon 20 through a few liquid dispensing apertures 106 distributed along the thrust tutor 82 in order to favour the evacuation of air bubbles and to avoid that the emptying of the balloon 20 be hindered when one of the apertures 106 is closed by the membrane of the balloon 20.

At the extremity opposed to the tip 34 of the balloon 20, the filling tube 22 extends exteriorly of the tutor 30 by the extension 23 of the filling tube 22 of the tight compartment 18. This extension 23 of the filling tube is a supple tubing closed at its extremity by the standard three-way valves 24 which are connected in series to receive the filling syringe 26, and a pressure gauge, if required. The extension 23 of the filling tube 22 facilitates the manipulations of the electrode balloon B.

In animal experimentation, the balloon 20 is allowed to be inflated with air but for a human being, in case of puncturing, air could infiltrate the coronary arteries and produce an embolism. Therefore, a saline solution is used for humans. The liquid being incompressible, the required volume for inflating the balloon 20 and the pressure exerted by the heart H on the balloon 20 can be measured.

When the balloon 20 is inflated in a cavity of the heart H, the heart contracts in an isometrical way against the incompressible volume of liquid, which does not hinder its functioning nor the perfusion of the myocardium 62.

The extremity of the thrust tutor 82 is fixed at the tip 34 of the balloon 20 with respect to which the electrodes 12 are identified. When the extremity of the tutor 30 reaches the bottom of the cavity in which the probe is introduced, we then know that the electrode balloon B is in place and that the electrodes 12 are well distributed within this cavity.

This joint combines and stabilizes the extremity of the thrust tutor 82, the knitting 10 and the rubber balloon 20. An insert 108 attached to the extremity of the tutor 30 offers a grip across the rubber balloon 20 for tying the knitting 10. A silk thread 110 which holds the insert 108 also solidifies the rubber plug 84 of the intubation guide compartment 31.

Having now described the structure of the present invention, we will address the aforementioned insertion restraints and the solutions thereto in view of the present electrode balloon B being used, for example, for measuring signals of the left ventricle 40. In response to these restraints, the present electrode balloon B presents the following characteristics:

a) The handle 37 extends the reach of the probe.

b) The balloon B is made of elastic materials (knitting 10 and rubber 20) which permit the electrode balloon to reach a sufficient inflated volume from little material whereby when deflated the balloon occupies little space for facilitating the insertion thereof.

c) The combination of a supple tutor 30 and of a more rigid intubation guide 32 of different materials offers a choice of consistence while restraining the diameter of the tutor.

d) The integration of the filling tube 22 to the tutor 30 also contributes to restrict the diameter of the probe.

e) The malleability of the intubation guide 32 is chosen in view of the form that must be given to the tutor 30 for working around the heart H in the rib cage; the material can also have a memory in order that the intubation guide 32 tends to straighten itself out after insertion in order not to offer resistance to the inflating or to the withdrawal of the balloon; on the other hand, it is supple enough in order not to force and pierce a wall of the heart.

f) The spherical shape electrode heads 12 and their close fastening against the knitting 10 prevents tears in the mitral valve cordages 50 and alterations to the endocardium 60.

g) In order to diminish the resistance to the insertion, the probe has a profiled and integrated exterior shape:
   1) The knitting 10 extends along the tutor 30 while enveloping the balloon/tutor joint and the electrode wiring harness 14;

2) The conducting wires 88 extend across the surface of the balloon B under the knitting 10; and 3) A thin and plane knitting 10 which does not go into lumps has been chosen. It is stretched by the thrust tutor 82 to avoid creases, pleats or wrinkles which would stick during insertion.

Figure 7:
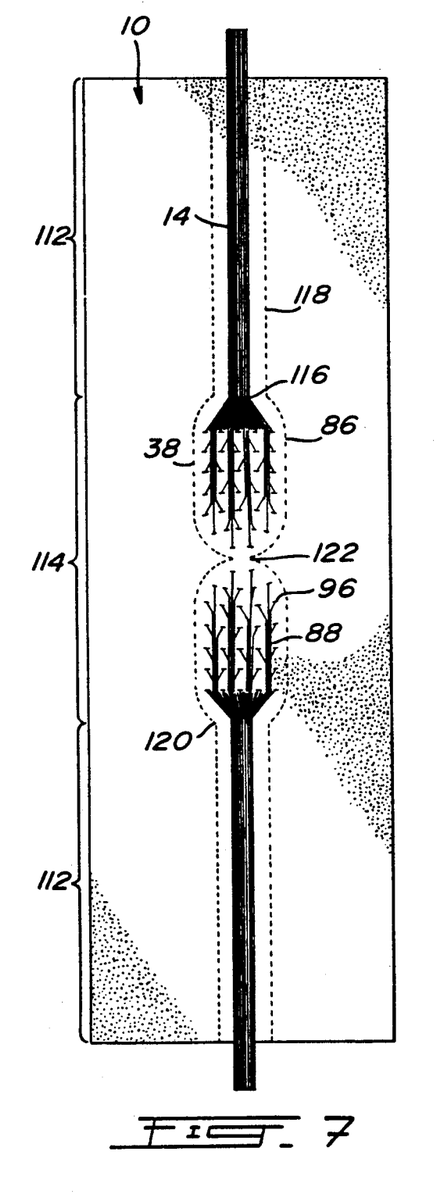
FIG. 7 is a schematic view showing the internal face of the electrode system prior to the cutting of the knitting and the assembly thereof to the tight compartment.

FIG. 7 illustrates a view of the internal face of the electrode system prior to the cutting of the knitting 10 and the assembly thereof to the tight compartment 18. The handle section of the electrode balloon B is indicated by 112 whereas the balloon section is indicated by 114. The emergence of the wires 88 from the balloon 20 is indicated by 116. The dotted lines 118 represent a marking guide for the cutting of the knitting and also indicates the site of the junction seams 38. Numerals 120 and 122 respectively represent the balloon base and tip regions.

The cutting of the knitting 10 and its assembly determines the shape and the maximum volume of the inflated balloon 20 intended therefor. The balloon 20 is dimensioned to obtain an electrode distribution which is regular, predictable and reproducible as well as a proper contact of all of its electrodes 12 on the cardiac surfaces being studied.

However, it is noted that the balloon takes its shape and that the cardiac muscle, in view of its suppleness, adjusts itself thereto, to a certain degree. This provides a certain maneuverability margin.

Descriptions of electrode balloons for the different cardiac chambers follow hereinbelow.

Figure 9:
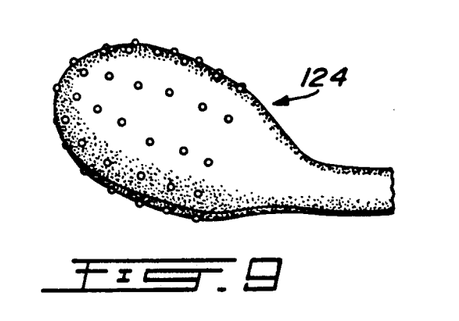
Figure 10:
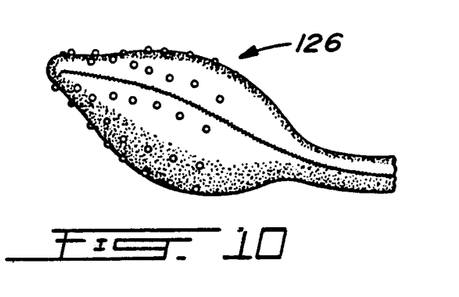

A detailed description of an electrode balloon for a left ventricle was given hereinbefore to which the following can be added. The left ventricle of a patient which has developed an aneurysm has a shape which differs from that of a normal ventricle. The cardiac cavity is then rounder and more domed. For these pathological cases in the human as well as in the dog, the balloons have an elongated oval or ellipsoid shape in the longitudinal direction of the probe. The human electrode balloon has the size of a kiwi fruit whereas an electrode balloon for the dog is smaller and has the size of a prune. FIGS. 9 and 10 show electrode balloons 124 and 126 adapted respectively for a pathological human's left ventricle and a normal human's left ventricle.

For hearts of normal dogs, the electrode balloon is cone-shaped and has the size of a strawberry.

The shape of the oval balloon is suitable to both an introduction through the aneurysm opening or through the mitral valve. In the first case, the tip of the balloon is lodged towards the mitral valve whereas in the other, the tip is directed towards the apex of the heart.

The majority of the existing endocardial probes for the left ventricle with aneurysm have the same oblong shape for both the human and the dog (Toronto, Chicago and Amsterdam balloons).

An electrode balloon intended for a right auricle is introduced through an incision in the right auricular appendix so that the tip of the balloon is lodged in the mouth of the inferior vena cava 80. This balloon has thus an oval shape and the format of the corresponding balloon for the left ventricle but with an outgrowth on its sides which fits into the tricuspid valve 54 in order to immobilize the electrode balloon in the cavity along a reproducible orientation. The shape of the balloon is therefore symmetrical along a sagittal plane.

Figure 8:
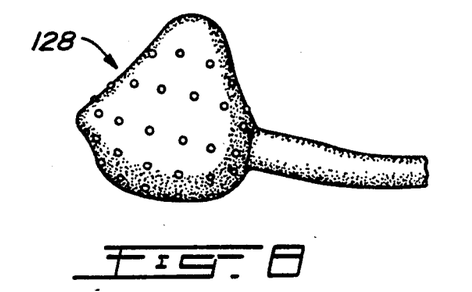
FIGS. 8 to 10 are perspective views showing different electrode balloons adapted respectively for a dog's right auricle, a human's left ventricle with aneurysm and a normal human's left ventricle.

An electrode balloon for the corresponding left auricle will have a shape similar to that of the right auricle although it will be a bit shorter. An electrode balloon 128 intended for a dog's right auricle is illustrated in FIG. 8.

While the left ventricle can be filled with the shape of a revolution, the right ventricle which has a tendency to envelope the left ventricle has the more complex shape of a curved triangular pyramid having its long axis parallel to that of the heart. The right ventricle 42 includes three walls, a summit and a base:

a) the front wall, slightly concave corresponds to the sternocostal face of the heart;

b) the inferior wall, slightly concave, corresponds to the diaphragmatic face of the heart;

c) the internal wall, very convex, is formed by the intraventricular septum 58;

d) a summit, in front, corresponds to the apex 66 of the heart; and e) the base, in back, which faces towards the auricles comprises the tricuspid valve 54 providing communication between the right auricle and the right ventricle, and the pulmonary valve 72 which regulates the communication of the right ventricle 42 to the pulmonary artery 70.

Functionally, the right ventricle 42 can be divided in two parts: an auricular portion called the inflow tract and an arterial portion called infundibulum or outflow tract. The inflow tract is delimited by the tricuspid valve 54 and the front and inferior walls of the cavity. It mainly communicates with the right auricle 46. Blood entering the inflow tract from the right auricle 46 is propelled at a 60° angle in the outflow tract which is wider than the inflow tract and which is funnel-shaped having its superior summit corresponding to opening of the pulmonary artery 70.

Figure 11:
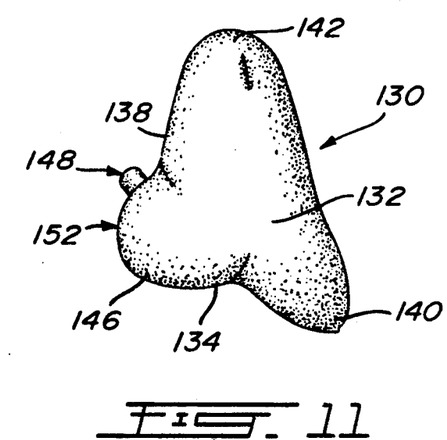
FIGS. 11 and 12 are front and interior perspective views of an electrode balloon adapted for a right ventricle without its electrode heads.
Figure 12:
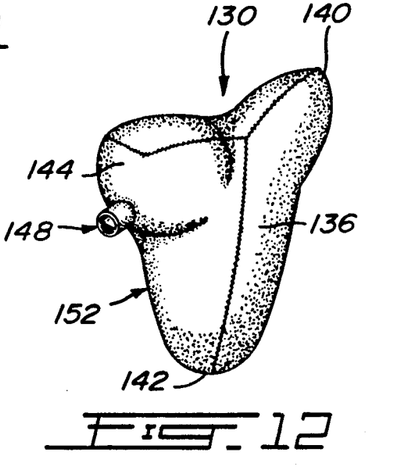

Globally, an electrode balloon for the right ventricle 42 is comparable to a tetrahedron, a solid geometric figure with four faces and four summits (triangular pyramid). FIGS. 11 and 12 illustrate such an electrode balloon 130 without the electrode heads, the handle and the full tutor thereof. The faces correspond to the walls of the ventricle described hereinabove. More particularly, these faces are:

a) a front face 132, convex, pressed against the front wall of the right ventricle;

b) an inferior or exterior face 134, pressed against the inferior wall;

c) an interior or septal face 136, slightly concave, pressed against the septum 58; and d) a posterior or basal face 138, pressed against the tricuspid valve 54.

The summits are:

a) an apical tip 140, located at the apex 66;

b) an arterial tip 142, longer, located in the arterial cone of the pulmonary artery; and c) the auricular tips 144 and 146, two close summits corresponding to the tricuspid valve 54.

The electrode balloon 130 comprises a voluminous part occupying the auricular portion of the right ventricle 42 and a thinner extension which fits in the arterial cone. As a whole, the electrode balloon 130 for the right ventricle 42 is flat and offers a concave curvature on its septal face.

Figure 13:
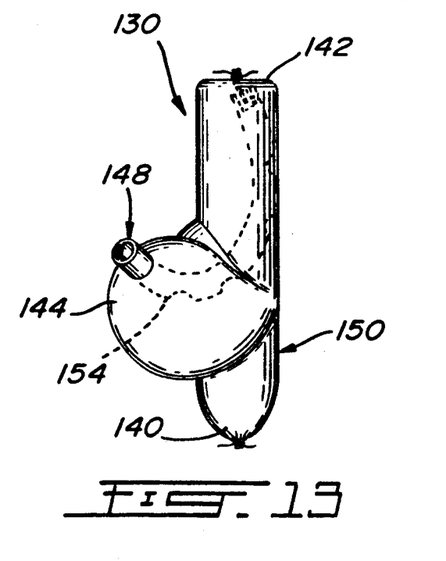
FIG. 13 is a bottom view of an electrode balloon for the right ventricle without its knitting.

FIG. 13 illustrates the electrode balloon 130 of FIGS. 11 and 12 for the right ventricle 42 without its knitting.

The form of the electrode balloon for the right ventricle complicated the exploitation of the principle of adduction of the electrodes by inflation since pneumatic structures tend to distribute the forces in a way such as their resulting shape is that of a sphere or a cylinder.

The inflatable volume was therefore compartmentalized. On the other hand, in order to maintain only one tight compartment, the long cylindrical balloon was folded upon itself which resulted in a protruding volume, slightly flat and concave (FIG. 13).

Two assembly methods for the tight compartment are possible.
1) The gluing on itself of the long rubber balloon folded inside its knitting envelope; and
2) A long balloon covered with a knitting and folded and sewn onto itself.

To facilitate the fabrication of the balloon, the first solution which is shown in FIG. 13 was preferred although both methods can produce adequate shapes.

The electrode balloon 130 for the right ventricle 42 is introduced through an incision in the right auricle 46 and through the tricuspid valve 54 thereby preserving the right ventricle 42. A tutor 148, curved by way of an intubation guide (not shown) which rigidifies it and renders it malleable, is pushed towards the pulmonary artery 70.

The tutor 148 is again a multifunctional vinyl tube to which is attached a rubber balloon 150 (FIG. 13) and a knitting 152 (FIGS. 11 and 12). The tutor 148 extends across the basal face 138 of the electrode balloon 130 and continues inside the balloon with the shape of a hook until it reaches the arterial tip 142 at which point it is fixed. As in the case of the electrode balloon B for the left ventricle 40, a thrust tutor 154, that is the part of the tutor 148 located inside the electrode balloon 130, maintains most of the knitting 152 in a stretched state during insertion. The apical tip 140, limp during insertion, shapes up when the balloon 130 is inflated.

The electrode balloon 130 for the right ventricle 42 comprises more material than the corresponding balloon B for the left ventricle 40 but the congestion during the insertion is less restricting in the first case since the approach is made from the front face of the heart.

It is noted that the tight compartment of all of the above electrode balloons can comprise a double rubber membrane although the illustrated balloons include only one such membrane and have proven operational.

If it is necessary to record the signals in a bipolar mode rather than in a unipolar one, the hereinabove described electrode heads need only to be replaced by bipolar heads.

The probe according to the present invention is reusable. It is washable with soapy water and sterilizable with gas. The probe can be dismantled in two parts: the electrode system on one hand and, on the other hand, the electrode adduction system and the tutor which form a single part. Therefore, when the tight compartment is not usable anymore, the electrode system which is more costly can be recuperated.

The electrode balloon described hereinbefore is a pick-up probe for electrophysiological signals applied to the recording of endocardial activation potentials in the left ventricle of the heart. As also shown hereinabove, this concept is adaptable to the other cardiac chambers such as the auricles and the right ventricle. It is therefore also possible that the electrode balloon according to the present invention may be adapted to other anatomical cavities where it is possible and interesting to record bioelectrical signals. This adaptation is done by simply modifying certain parameters of the probe such as the length of the tutor, the quantity of electrodes, the pattern of the knitting, etc.

It is noted that the spherical bearings or electrodes, the knitting, the tube from which originates the tutor, the conducting wires and the rubber balloons are all commercially distributed for different uses.

The above described electrode balloon is presently manufactured under small scale production and rather craftsmen-like methods. Therefore, the choice of the available processes has surely influenced the conceptualization of the probe, but the hereinabove presented principles could eventually be adapted for mass production. A few design modifications would then be required. For example, the rubber balloon would be replaced by another material, the knitting and the balloon could be melted or fused to the tutor, the hereinabove described knitting could be replaced by another knitting or by an equivalent material having the same properties but better suited to industrial processes. The above-concept of a tutor with an inflated balloon and with an electrode carrier having a tridimensional structure would still apply.

A new surgical technique and the unavailability on the market of an electrode system necessary to perform this surgery justifies the herein presented improvement of the electrode balloon concept.

With respect to previous products which were the object of publications, the herein described innovations relate to the structure of the probe, the tutor and the tight compartment; the electrode heads and their connection to the conducting wires; the fastening of the electrode heads to their support; the choice and the construction of the electrode supports; as well as the design details resulting from the hereinabove enumerated structural elements.

The aforementioned publication introducing the Toronto balloon basically limits the structural description thereof to the electrode carrying expandable mesh. The internal structure of the Toronto balloon responsible for the inflation and deflation thereof as well as for its guidance is not described. In the Toronto balloon, an expandable mesh is used to carry the electrodes and to cover a double membrane latex balloon.

In the present invention, a knitting is used instead of an expandable mesh and the distinction therebetween is important as it will be shown hereinafter. Indeed, the present knitting introduces significant improvements to the electrode balloon field in relation to the expandable mesh of the Toronto balloon.

One of these improvements is reliant on the assembly of the knitting which determines the shape of the different electrode balloons conceived for each of the four heart cavities of the dog as well as of the human. The different balloon shapes described hereinbefore were the subject of a series of tests and prototypes before resulting in definite and very functional models.

The present electrode balloon meets the insertion constraints of a narrow passage which is encountered for the left ventricle and for the other cardiac chambers (right ventricle and right and left auricles), but at different levels. Consequently, the inflatable balloon concept, from a compact to a spread out volume, is not only applicable to the left ventricle but also to the other cavities, with some adjustments to the shape as previously seen.

In this case, the selected knitting to cover the balloon is very suitable. Its functions are to carry the set of electrodes in a predetermined distribution or arrangement and to impose a shape to the inflated balloon, all while hindering in a minimal way the insertion and the withdrawal of the balloon.

The knitting is made of a commercial material which is extensible and resistant (LYCRA), which is nylon and elastomer-based (SPANDEX). Although this type of knitting is commercially available, its particular present application is original and introduces important advantages to the electrode balloon. The various properties of the knitting are presented hereinbelow.

The choice of the electrode carrier lies on a well-balanced elasticity in view of which follow most of the advantages of the knitting in relation to the latex membrane of the Amsterdam balloon or to the expandable mesh of the Chicago and Toronto balloons.

Knittings possess an intrinsic elasticity conferred by their tridimensional structure. The combination of this structure with the Spandex enhances the material's return force. Then, the tensions are better distributed and the elongation is made uniform. Consequently, the knitting stretches with regularity, moderation and reproducibility, contrary to an expandable mesh too easily stretched and deformed.

We thus avoid torsions and distortions while the balloon is being partially or totally inflated in spite of the fact that the underlying rubber balloon may distend with irregularity, or that external factors constrain the knitting's deployment.

Three important consequences result from the knitting's elasticity. First, even if the knitting is twisted during insertion, the electrodes will spread out during the inflation of the balloon with the necessary regularity and reproducibility so that the mapping of the activation potentials corresponds to the endocardial distribution of the electrodes, and so as to estimate the anatomical localization of the electrodes when the balloon is hidden in the cardiac chamber.

Second, the form of the balloon is determined based on the cut-out of the knitting and on its assembly. This way, the balloon conforms with the cavity for which it is intended. Balloons of proper shapes can thus be obtained for the ventricles or the auricles of both animals or humans, normal or diseased.

Third, the volume of the electrode balloon adjusts itself to the variability of the cardiac cavities which are encountered from one patient to another. More or less inflated, the balloon offers a wide enough range of functional volumes within which the deployment of the electrodes is regular and reproducible.

These above characteristics are not found in the other existing electrode balloons which all offer an inadequate extensibility margin. While experimenting, it became obvious and important that the deflated balloon does not include an excess of limp material which creases and obstructs or which gets stuck in the anatomical structures during insertion. For this reason, the knitting is kept tight, slightly stretched, by the extension of the tutor to the distal end of the balloon. This also prevents the knitting from twisting during insertion.

The above is made possible by the relatively moderate longitudinal extensibility of the knitting and to its sufficient transverse extensibility whereby the knitting can spread out properly and sufficiently from a small amount of material.

The intubation guide, that is the stem made of a malleable material which is introduced in one of the channels of the tutor in order to rigidify the same, allows for the knitting's tension to be varied. The thrust tutor being longer than the knitting which surrounds it, the knitting stretches as much as possible as the intubation guide is introduced in the tutor. During inflation, the intubation guide is removed and the thrust tutor bends inside the balloon thereby not impeding the longitudinal retreat or contraction which accompanies the deployment.

The Toronto balloon not having this internal structure nor these mechanical properties, its expandable mesh becomes limp when it is deflated for insertion, with all the consequent inconveniences. When the positioned balloon remains twisted when inflated, it is necessary to repeat the insertion. The elasticity level of the expandable mesh does not guarantee the regular deployment of the electrodes.

The knitting offers other advantages which are succinctly introduced hereinafter. The fully stretched knitting limits the inflating of the balloon to a predetermined volume. The knitting is thin and elastic whereby a limited amount thereof is sufficient to cover the totality of the balloon. This contributes in minimizing the transverse section of the deflated balloon and thus the friction during insertion.

The fine and close stitches of the knitting provide for a continuous surface which offers latitude regarding the disposition and the number of electrodes carried thereby in relation to a mesh which can only accommodate certain arrangements.

The close stitches of the knitting protect the balloon from punctures, for instance, from a mishandling of a lancet. The knitting's fine texture offers low friction during insertion in comparison to a very textured mesh. Moreover, if the knitting is gashed, it does not fray. These characteristics make for a durable material.

The nylon provides the knitting with a large tensile resistance which allows it to support an excessive inflating. The knitting resists very well to abrasion. Furthermore, the knitting does not have a tendency under friction to form thereon small fiber balls which could loosen and move to the circulatory system of the patient. On the other hand, if tiny fibers detach from the knitting, they would be recuperated by aspiration of the rinsing saline solution.

The fixation mode of the electrode heads to the above knitting is well suited for an insertion through the mitral valve. On the other hand, the electrodes carried on the Amsterdam balloon are machined silver balls maintained in apertures defined in the support of the latex. The solidity of such an electrode fixation would be insufficient for an insertion through the mitral valve since it depends on the resistance of the latex and of the weld joining the ball to its conducting wire. The inserts of the Chicago balloon which carry in pairs the electrode balls are adapted for an insertion directly in the ventricle as an insertion through the mitral valve would be clinging.

The Amsterdam and Chicago balloons are thus introduced in the heart by ventriculotomy only. They do not have the structural consistence for an insertion through the left auricle, nor adequate electrode connections. In both these cases, the electrode distribution is regular within a very limited range of formats. Therefore, the adaptation of these balloons to different volumes of cavities is compromised.

Finally, the present electrode balloon and, more particularly, the electrode carrying knitting thereof provides for the following advantages with respect to the Toronto balloon at the following levels: smaller insertion diameter, adjustability to different cardiac cavity volumes and better durability.

To this date, the electrode balloon has been used many times in the operating room and on dogs. It has satisfied very well the requirements of operative protocols, which demonstrate the functionality of the developed innovations.

I claim:

1. An electrode balloon for use in anatomical cavities for picking up bioelectrical signals from walls thereof simultaneously in a multitude of sites for the mapping of activation potentials thereof, comprising an inflatable tight member defining a chamber and having an opening at a proximal end thereof in connection with a flexible tube; an extensible cover means covering at least said chamber and provided with a plurality of sensor electrodes distributed thereon for contacting the walls of a cavity when said inflatable member is inflated by a fluid conveyed through said tube into said chamber; insulated electrical conductors connected to said sensor electrodes and adapted for connection to means for recording and processing the signals picked up thereby; a flexible tutor means extending within said chamber from a distal end of said inflatable member through and past said proximal end thereof for providing said electrode balloon with a handle; and a flexible intubation guide means adapted to be received in said tutor means and adapted for conferring a shape to said tutor means for facilitating an insertion of said inflatable member into the cavity, said cover means being adapted for conferring to said inflatable member a shape similar to that of the cavity.

2. An electrode balloon as defined in claim 1, wherein said tube is integral with said tutor means for at least a length of said tube interior of said chamber whereby said tube and said tutor means define respectively first and second separate elongated compartments for receiving respectively the fluid and said intubation guide means, at least an aperture being provided in said tube within said chamber for dispensing the fluid provided therein in said chamber.

3. An electrode balloon as defined in claim 2, wherein said inflatable member comprises a rubber balloon.

4. An electrode balloon as defined in claim 3, wherein said cover means is a knitting made of an extensible and resistant material constituted of closely stitched fine threads.

5. An electrode balloon as defined in claim 4, wherein said extensible and resistant material comprises a nylon and elastomer material.

6. An electrode balloon as defined in claim 5, wherein said elastomer material is spandex.

7. An electrode balloon as defined in claim 6, wherein said spandex is Lycra TM.

8. An electrode balloon as defined in claim 4, wherein a connection means is provided for interconnecting said knitting, said rubber balloon, said tutor means and said tube at distal ends thereof.

9. An electrode balloon as defined in claim 8, wherein said connection means comprises a rubber plug fitted at said distal end of said tutor means in said compartment thereof, an insert provided at said distal end of said rubber balloon, and a connection thread joining said rubber plug and said insert.

10. An electrode balloon as defined in claim 4, wherein a silicone ring is provided around a proximal end section of said rubber balloon between said knitting and said rubber balloon for tightening said rubber balloon against said tutor means and said tube, whereby the fluid can only be supplied to and evacuated from said chamber through said aperture of said tube.

11. An electrode balloon as defined in claim 10, wherein said rubber balloon is also glued to said tutor means and to said tube at said proximal end section thereof.

12. An electrode balloon as defined in claim 4, wherein each one of said sensor electrodes is a hollow ball mounted exteriorly on said knitting, a pair of openings being diametrically defined in said hollow ball for receiving therethrough a thread which passes through said knitting adjacent said hollow ball, said hollow ball being secured to said knitting by said thread being knotted intermediate said knitting and said rubber balloon.

13. An electrode balloon as defined in claim 12, wherein a slot is defined in a portion of said hollow ball facing said knitting, and at least partly bearing thereagainst, one of said electrical conductors passing through said slot and having a bared free end thereof located in said hollow ball and contacting an inner surface thereof, said electrical conductor being knotted within said hollow ball adjacent said slot thereby securing said bared free end inside said hollow ball and ensuring a contact therebetween, said electrical conductor extending from said hollow ball through said knitting, past said proximal end of said rubber balloon and towards the means for recording and processing the signals picked up by said sensor electrodes.

14. An electrode balloon as defined in claim 13, wherein said hollow ball and said electrical conductor are both made of stainless steel thereby avoiding junction potentials.

15. An electrode balloon as defined in claim 4, wherein said rubber balloon comprises a pair of juxtaposed membranes.

16. An electrode balloon as defined in claim 4, wherein said knitting extends from said distal end of said rubber balloon past said proximal end thereof and at least partly onto said handle so as to envelope thereat said tutor means, said tube and said electrical conductors which all emerge from said knitting at a proximal end thereof.

17. An electrode balloon as defined in claim 4, wherein said knitting is a cut-out adapted for conferring to said rubber balloon, when inflated, a shape similar to that of the cavity, said cut-out being joined around said rubber balloon and around said tutor means and said tube at said handle by junction seams.

18. An electrode balloon as defined in claim 17, wherein said cut-out is also glued to said tutor means and to said tube at said handle.

19. An electrode balloon as defined in claim 17, wherein at least a guiding mark seam is provided on a section of said knitting overlying said rubber balloon intermediate said proximal and distal ends thereof for guiding the positioning of said rubber balloon in the cavity in order to correctly extrapolate the relative positioning of said sensor electrodes on the walls thereof thereby ensuring a proper cartography of the signals picked up therefrom.

20. An electrode balloon as defined in claim 2, wherein said tutor means and said tube are made of PVC.

21. An electrode balloon as defined in claim 2, wherein said intubation guide means is a malleable stem made of metal or of a plastics material.

22. An electrode balloon for use in anatomical cavities for picking up bioelectrical signals from walls thereof simultaneously in a multitude of sites for the mapping of activation potentials thereof, comprising an inflatable tight member defining a chamber; means connected to said chamber for filling the inflatable tight member; an extensible knitting constituted of closely stitched fine threads covering at least said chamber and provided with a plurality of sensor electrodes distributed thereon for contacting the walls of a cavity when said inflatable member is inflated by a fluid conveyed through said means for filling into said chamber; conductor means connected to said sensor electrodes and adapted for connection to a means for recording and processing the signals picked up thereby; and a flexible handles extending from said chamber for guiding said inflatable member into the cavity, said knitting being adapted for conferring to said inflatable member a shape similar to that of the cavity.

23. An electrode balloon as defined in claim 22, wherein said means for filling is an elongated tube, a proximal end of said inflatable member defining an opening in connection with said tube.

24. An electrode balloon as defined in claim 23, wherein said handle means comprises an elongated tubular tutor extending within said chamber from a distal end of said inflatable member through and past said proximal end thereof, said handle further comprising a flexible intubation guide adapted for insertion in said tutor for positioning said inflatable member into the cavity.

25. An electrode balloon as defined in claim 24, wherein said tube is integral with said tutor, for at least a length of said tube interior of said chamber, whereby said tube and said tutor define respectively first and second separate elongated compartments for receiving respectively the fluid and said intubation guide, at least an aperture being provided in said tube within said chamber for dispensing the fluid provided therein in said chamber.

26. An electrode balloon as defined in claim 25, wherein said intubation guide is a malleable stem made of a metal or of a plastics material.

27. An electrode balloon as defined in claim 25, wherein said tutor and said tube are made of PVC.

28. An electrode balloon as defined in claim 25, wherein said inflatable member comprises a rubber balloon.

29. An electrode balloon as defined in claim 28, wherein said knitting comprises a nylon and elastomer material, the elastomer material comprising spandex.

30. An electrode balloon as defined in claim 29 wherein said spandex is lycra TM.

31. An electrode balloon as defined in claim 28, wherein a connection means is provided for interconnecting said knitting, said rubber balloon, said tutor and said tube at distal ends thereof.

32. An electrode balloon as defined in claim 31, wherein said connection means comprises a rubber plug fitted at said distal end of said tutor in said compartment thereof, an insert provided at said distal end of said rubber balloon, and a connection thread joining said rubber plug and said insert.

33. An electrode balloon as defined in claim 28, wherein a silicone ring is provided around a proximal end section of said rubber balloon between said knitting and said rubber balloon for tightening said rubber balloon against said tutor and said tube, whereby the fluid can only be supplied to and evacuated from said chamber through said aperture of said tube.

34. An electrode balloon as defined in claim 33, wherein said rubber balloon is also glued to said tutor and to said tube at said proximal end section thereof.

35. An electrode balloon as defined in claim 28, wherein said conductor means comprise insulated electrical conducting wires, and wherein each one of said sensor electrodes is a hollow ball mounted exteriorly on said knitting, a pair of openings being diametrically defined in said hollow ball for receiving therethrough a thread which passes through said knitting adjacent said hollow ball, said hollow ball being secured to said knitting by said thread being knotted intermediate said knitting and said rubber balloon.

36. An electrode balloon as defined in claim 35, wherein a slot is defined in a portion of said hollow ball facing said knitting and at least partly bearing thereagainst, one of said conducting wires passing through said slot and having a bared free end thereof located in said hollow ball and contacting an inner surface thereof, said conducting wire being knotted within said hollow ball adjacent said slot thereby securing said bared free end inside said hollow ball and ensuring a contact therebetween, said conducting wire extending from said hollow ball through said knitting, past said proximal end of said rubber balloon and towards the means for recording and processing the signals picked up by said sensor electrodes.

37. An electrode balloon as defined in claim 36, wherein said hollow ball and said conducting wire are both made of stainless steel thereby avoiding junction potentials.

38. An electrode balloon as defined in claim 28, wherein said rubber balloon comprises a pair of juxtaposed membranes.

39. An electrode balloon as defined in claim 28, wherein said knitting extends from said distal end of said rubber balloon past said proximal end thereof and at least partly onto said handle so as to envelope thereat said tutor, said tube and said conductor means which all emerge from said knitting at a proximal end thereof.

40. An electrode balloon as defined in claim 28, wherein said knitting is a cut-out adapted for conferring to said rubber balloon, when inflated, a shape similar to that of the cavity, said cut-out being joined around said rubber balloon and around said tutor and said tube at said handle by junction seams.

41. An electrode balloon as defined in claim 40, wherein said cut-out is also glued to said tutor and to said tube at said handle.

42. An electrode balloon as defined in claim 40, wherein at least a guiding mark seam is provided on a section of said knitting overlying said balloon intermediate said proximal and distal ends thereof for guiding a positioning of said rubber balloon in the cavity in order to correctly extrapolate relative positioning of said sensor electrodes on the walls thereof thereby ensuring a proper cartography of the signals picked up therefrom.

43. A method for picking up bioelectrical signals from the walls of anatomical cavities simultaneously in a multitude of sites for the mapping of activation potentials thereof, comprising the steps of:
a) providing an electrode balloon comprising an inflatable tight member defining a chamber and having an opening at a proximal end thereof in connection with a flexible tube, an extensible cover means covering at least said chamber and provided with a plurality of sensor electrodes distributed thereon,, insulated electrical conductors connected to said sensor electrodes and to a means for recording and processing the signals picked up thereby, and a flexible tutor means extending within said chamber from a distal end of said inflatable member through and past said proximal end thereof for providing said electrode balloon with a handle;

b) introducing in said tutor means a flexible intubation guide adapted for conferring a shape thereto for facilitating an insertion of said inflatable member into a cavity of a patient;

c) inserting said inflatable member into the cavity;

d) supplying a liquid through said tube in said chamber for inflating said inflatable member, whereby said cover means confers to said inflatable member a shape similar to that of the cavity and said sensor electrodes contact walls of the cavity; and e) picking up by way of said sensor electrodes the bioelectrical signals of the walls of the cavity simultaneously in a multitude of sites.

44. A method as defined in claim 43, wherein said inflatable member is introduced in the left ventricle of a heart through the mitral valve thereof with said handle extending from said inflatable member through the mitral valve and the left auricle of the heart.

45. A method for picking up bioelectrical signals from the walls of anatomical cavities simultaneously in a multitude of sites for the mapping of activation potentials thereof, comprising the steps of:

a) providing an electrode balloon comprising an inflatable tight member defining a chamber, a flexible filling means connected to said chamber, an extensible knitting constituted of closely stitched fine threads covering at least said chamber and provided with a plurality of sensor electrodes distributed thereon, conductor means connected to said sensor electrodes and connected to a means for recording and processing the signals picked up thereby, and a flexible tubular handle extending from said chamber;

b) introducing in said handle a flexible intubation guide adapted for conferring a shape thereto for facilitating an insertion of said inflatable member into a cavity;

c) inserting said inflatable member into the cavity;

d) supplying a liquid by way of said filling means in said chamber for inflating said inflatable member, whereby said knitting confers to said inflatable member a shape similar to that of the cavity and said sensor electrodes contact walls of the cavity; and e) picking up by way of said sensor electrodes the bioelectrical signals of the walls of the cavity simultaneously in a multitude of sites.

46. A method as defined in claim 45, wherein said inflatable member is introduced in the left ventricle of a heart through the mitral valve thereof with said filling means and said handle extending from said inflatable member through the mitral valve and the left auricle of the heart.

* * * * *